United States Patent [19]

Topham

[11] 3,985,122

[45] Oct. 12, 1976

[54] MULTI-PISTON SYRINGE DEVICE

[75] Inventor: Silas Charles Topham, Orem, Utah

[73] Assignee: Medical Development Corporation, Salt Lake City, Utah

[22] Filed: June 4, 1975

[21] Appl. No.: 583,776

[52] U.S. Cl. ............................ 128/2 F; 128/218 M; 128/218 P
[51] Int. Cl.$^2$ ......................................... A61B 5/00
[58] Field of Search ............ 128/2 F, 213, 214, 215, 128/218 R, 218 P, 218 M, 234, 220, 221

[56] References Cited
UNITED STATES PATENTS

| | | | |
|---|---|---|---|
| 3,016,896 | 1/1962 | Van Sickle | 128/218 M |
| 3,477,431 | 11/1969 | Walecka | 128/218 M |
| 3,511,239 | 5/1970 | Tuschnoff | 128/218 M |
| 3,749,084 | 7/1973 | Cucchiara | 128/2 F |
| 3,766,917 | 10/1973 | Wimmer | 128/218 M |
| 3,881,484 | 5/1975 | Gidcumb, Jr. | 128/218 M |

FOREIGN PATENTS OR APPLICATIONS

| | | | |
|---|---|---|---|
| 1,214,053 | 12/1970 | United Kingdom | 128/218 M |

*Primary Examiner*—John D. Yasko
*Attorney, Agent, or Firm*—Fitch, Even, Tabin & Luedeka

[57] ABSTRACT

A syringe device having smaller and larger, coaxially aligned cylinder bores each provided with respective pistons. The larger rearmost piston is in slidable sealing engagement with its bore but is free-floating on the syringe plunger shaft so that as the forward piston is withdrawn the plunger shaft slips centrally through the rear piston. Thus, fluid drawn in by the forward piston is ultimately mixed with any contents of the large cylinder or bore associated with the larger piston. The rearward piston is free to adjust its disposition on the plunger shaft in response to positive fluid pressure existing forwardly thereof. At a predetermined point in the rearward travel of the plunger, during withdrawal strokes, the pistons are linked together by provided structure for enabling simultaneous, corresponding forward travel to eject the combined substances from the over-all syringe construction. The structure also admits of anerobic culture usage and, further, permits the subsequent selected mixing of independent chemical solutions which are pre-filled in the syringe. Many uses, advantages and design advances are present herein, which will be hereinafter discussed in detail.

2 Claims, 15 Drawing Figures

MULTI-PISTON SYRINGE DEVICE

The present invention relates to syringe constructions and, more particularly, to a syringe device which may be used for substance-mixing purposes in the manner hereinafter pointed out.

In many types of phsiological endeavors, such as sampling, laboratory testing, culturing, and so forth, in both human and also veterinary fields, it becomes necessary or appropriate to withdraw a fluid such as blood into a sterile cavity and to mix the same with another fluid or even a powdered chemcial, by way of example, previously introduced into the syringe. All of this needs to be performed under anerobic conditions within the withdrawal device, i.e. syringe, without the possibility of introducing contaminants.

The present invention supplies such a mixing syringe, with the same including plural, concentrically arranged cylindrical bores having respective pistons. The most forward bore near the canula is of reduced cross-section, whereas the rearmost bore contiguous therewith is of enlarged cross-section.

In the invention the foremost piston is keyed to the plunger shaft, whereas the rearmost piston floats thereon so that the shaft may be withdrawn rearwardly without disturbing the position of such rearmost piston. The rearmost piston of course will adjust its disposition on the plunger shaft in response to any positive fluid pressure existing at its forward surface.

Accordingly, the forward piston is used to withdraw fluids, such as blood, from a patient through the cannula and inwardly to the smaller bore area. Certain bypass apertures are provided which, when unsealed by the foremost piston, can operate to reduce the degree of negative pressure forwardly of the forward piston, thereby preserving the integrity of the blood cells drawn in and also for aiding the further withdrawal of a forward piston from its bore. A temporary stop or detent means is provided relative to the forward piston so that one may "feel" when an intermediate extremity of travel has been reached, thereby enabling the operator to know when a predetermined amount of fluid has been drawn from a patient.

The device is so constructed such that a further and continued withdrawal of the forward piston will ultimately produce a loacking, directly, or indirectly, of the forward piston with the rear piston such that the rear piston may be urged forwardly with the forward piston upon a return stroke of the plunger.

The device is suitable for mixing body fluid with a chemical solution or even with a powder disposed forwardly of the rearmost enlarged piston. The device can be used in culture, diagnostic, or other procedures, and the mixing and culturing can take place under anerobic conditions without any danger whatever of contamination or leakage. The syringe may also be prefilled with two different solutions that can subsequently be mixed through plunger withdrawal.

Accordingly, a principal object of the present invention is to provide a new and improved syringe device usable for mixing purposes as well as for other uses.

An additional object is to provide a syringe device having multiple or plural cylinder bores, preferably concentrically disposed, with the rearmost bore being of the larger crosssectional area, both bores being provided with respective pistons, the rearmost one being self-adjusting in response to the presence of fluid pressure.

An additional object is to provide a mixing syringe wherein incoming fluid can be mixed with a predisposed chemical solution contained centrally within the syringe.

A further object is to provide a syringe device which is pre-filled with separate solutions capable of being subsequently mixed at a predetermined time.

A further object is to provide a device to effect the anerobic storage, mixture, and culture of solutions of various types.

A further object is to provide a mixing syringe such that any chemical solution or even dry chemicals will not be mixed with any withdrawn or incoming fluid prior to the time the syringe is actually withdrawn from the patient subject and substance mixing is desired.

A further object is to provide a multi-cylinder bore syringe construction wherein the pistons therein are linked only on forward strokes of the supplied plunger.

The features of the present invention which are believed to be novel are set forth with particularity in the appended claims.

The present invention, both as to its organization and manner of operation, together with further objects and advantages thereof, may best be understood by reference to the following description, taken in connection with the accompanying drawings in which:

FIG. 1 is a perspective view of the syringe device of the invention in a preferred embodiment thereof.

FIG. 2 is a longitudinal, vertical section taken along the line 2—2 in FIG. 1.

FIG. 3 is similar to FIG. 2 but illustrates the plunger as having been withdrawn so that the forward piston approaches the rearward piston.

FIG. 4 is an enlarged transverse section taken along the line 4—4 in FIG. 2 and illustrates the configuration of the forward piston and its engagement with the enlarged head of the plunger shaft.

FIG. 5 is an enlarged, sectional detail taken along the line 5—5 in FIG. 2 and illustrates the prospective passage of the enlarged carrier portion of the plunger shaft through an eccentrically drilled washer, so that the shoulder of the carrier portion will assume a thrusting engagement with such washer preparatory to a forward thrust of both pistons by the plunger.

FIG. 5A is a section, taken along the line 5A—5A in FIG. 5, illustrating the configuration of the thrust-like washer and its relationship to the enlarged carrier portion of the shaft, in accordance with the positioning in FIG. 5 of such structure.

FIG. 6A is similar to FIG. 5A, is a section taken along the line 6A—6A, and illustrates the thrust washer and carrier portion in their mutual relationship when the disposition of the structure shown in FIG. 6 takes place.

Figure 7:
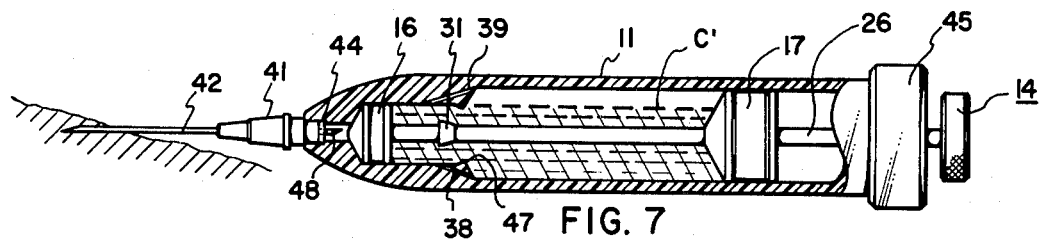
FIGS. 7–10 illustrate in side elevation the operation of the structure progressively, i.e. in withdrawing fluid from a patient to the mixing stage, allowing the so-withdrawn fluid to be mixed with any chemicals or fluid contained within the syringe, and finally, ejecting (FIG. 10) such mixed fluid through the replaced cannula.

In the drawings, and particularly FIGS. 1 and 2, the syringe device 10 is shown to include a cylinder housing 11 provided with coaxial, contiguous, forward and rearward cylindrical bores 12 and 13.

Plunger 14 is provided with an end, thumb-depression knob 15 and also forward and rear pistons 16 and 17. Plunger at 14 includes an enlarged head 18, see FIG. 4, which is thrust into a correspondingly shaped depression 19 in forward, resilient, sealing piston 16. Both pistons have sealing lands 20–23 for sealing against the interior walls of the respective cylinder bores.

These pistons are elastomeric and offer a radial compression seal against the interior bore walls.

A further reason for the elastomeric nature of rear piston 17 is illustrated in FIGS. 5 and 6. It is noted that such piston is provided with a conical hollow interior 24 which extends to an annular or circular, recessed seat 25 that is coaxial with the axis of the piston and of plunger shaft 26. An annular shoulder 27 is supplied proximate the terminal aperture 28 of the piston. Element 29 comprises a round washer having an eccentric aperture 30. Shaft 26 is provided with a concentric, tapered, enlarged, piston-carrier portion 31. Portion 31, during its course or rearward travel as the plunger 14 is withdrawn rearwardly, see FIG. 2, operates to proceed through the aperture 30 and, during such relative travel, cams upwardly the washer in the direction as shown by arrow 34, operating upon resilient elastomeric portion 35 of piston 17. After the carrier portion 31 has proceeded completely through the aperture, then the elastomeric nature of the piston at 35, see FIG. 6, operates to provide a restoring force so that such washer portion is restored downwardly; the thrust shoulder 37 is thereby enabled to press the washer forwardly and hence urge forwardly the entire piston construction at 17.

If desired, cylindrical housing 11 may include bypass apertures 38 and 39 for purposes hereinafter described.

Cylindrical housing 11 includes a front opening 40 for receiving the conventional cannula mount 41, the latter being provided with cannula needle 42. The rear portion of the cannula at 43 of course will communicate directly into the opening 40 and may be designed to pierce diaphragm 44 in the customary manner. The precise cannula construction and syringe barrel, resilient seal 44, closable upon cannula separation (see FIG. 10) automatically, are common in the art.

To close the rear of the cylinder housing there is provided a cap 45 that is screw-threaded onto the threads 46 of cylinder housing 11.

As to the forward cylinder bore 12, the same is coterminous with an annular ridge 47 which serves as an abutment ridge to limit temporarily the rearward travel of forward piston 16.

The operation of the structure as shown in FIGS. 7 thru 13 will now be described.

Preliminarily, the cannula unit at 41 will be supplied, the rear extremity thereof pushed through seal 44 so that the tip 48 of the canula communicates with the interior of cylinder housing 11. The canula needle 42 is thrust into the arm or another part of the body of a patient, for example, and plunger 14 is withdrawn, see FIG. 8, so that blood will enter and fill bore 12. The withdrawal of the plunger, in effecting a withdrawal of the forward piston 16, causes such piston to abut the chamfered stop ridge 47, see FIG. 8. The stop ridge in fact comprises a measuring detent so that when the same is reached a predetermined calibrated amount of fluid will have been drawn to be included within the cavity C in FIG. 8.

As the plunger is further withdrawn, the piston 16 will open the side passageways 38 and 39. These serve two purposes. First, the same reduces the negative pressure to the left of the forward piston 16 so as to preclude a chance of the rupturing of blood cells that have been withdrawn. Secondly, such negative pressure is reduced, through the fluid flow, from right to left, through such passageways 38 and 39 thereby facilitating and easing the further withdrawal of bore piston 16.

Figure 8:
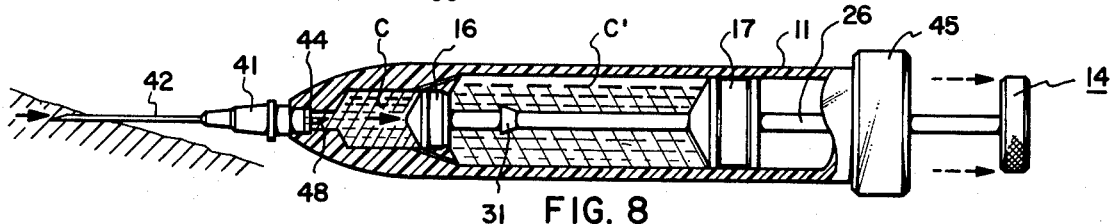
Figure 9:
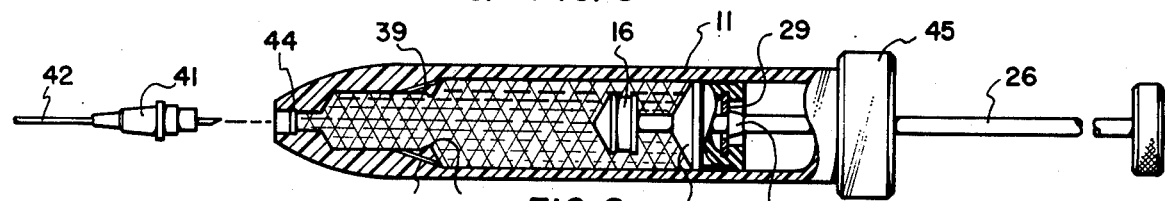

It is noted that during this entire operation floating piston 17 will remain in its predetermined position, see FIGS. 2, 7 and 8, owing to the slippage of plunger shaft 26 through axial aperture A of FIG. 6. Of course, piston 17 will be free to adjust in response to positive fluid pressure that may exist forwardly thereof. The enlargement of carrier portion 31 will approach progressively the elastomeric piston 17 and finally pass through the central eccentric aperture 37 of thrust washer 29. This operation will be accompanied by the thrusting outwardly of washer 29 against portion 36 of the piston 17 in FIG. 6, thereby aiding the carrier portion 31 to proceed through the washer's eccentric aperture and proceed therepast to the position shown in FIGS. 6 and 6A and also in FIG. 10. Accordingly, regardless of the axial or circumferential orientation of the rod, the abutment will proceed through the washer one way, but thereafter will be operative, via thrust shoulder 37, to urge the piston 17 forwardly. It is noted that the washer is seated in groove 25 in FIG. 5.

Figure 10:
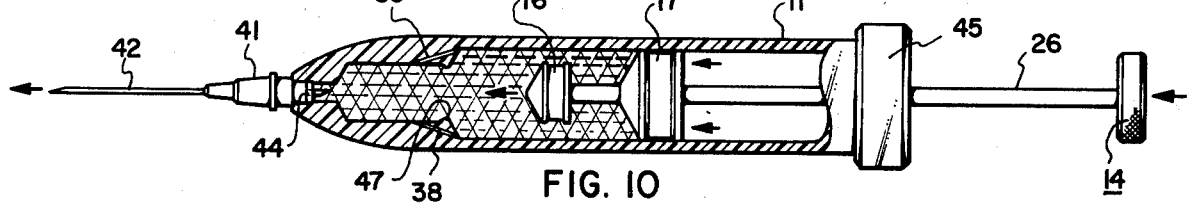

Once there has been a withdrawal of piston 16 past bore 12, then the blood or other body fluid that has been withdrawn and any solution or chemical (solid) as might be contained in cavity C', see FIG. 8, can be mixed as in FIG. 10 and subsequently ejected into a test tube, on a test slide, and so forth.

Figure 11:
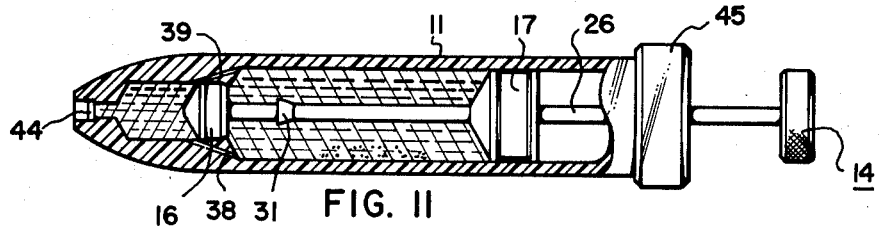
FIGS. 11–13 are similar to FIGS. 7–10 but illustrate a further operating sequence, hereinafter to be described.
Figure 12:
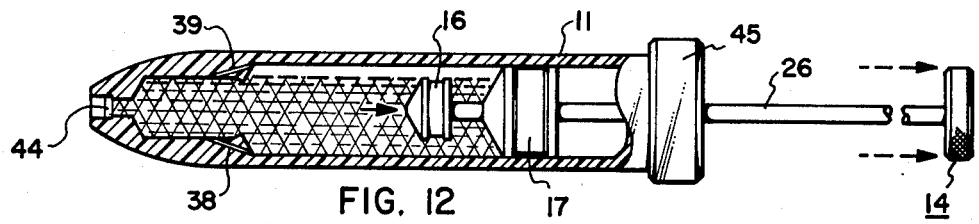
Figure 13:
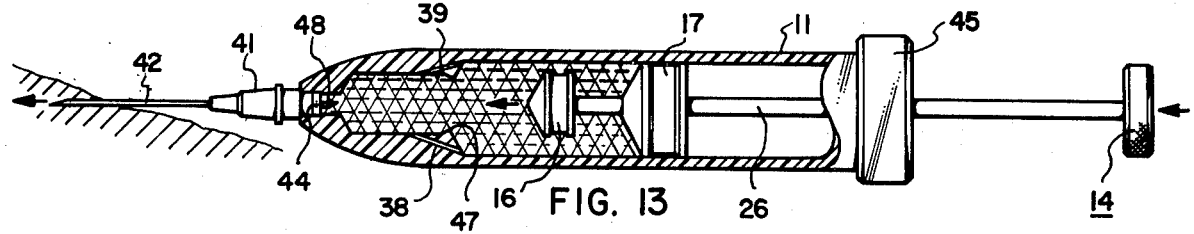

FIGS. 11–13 illustrate that the same procedure may be followed as that shown in FIGS. 7 thru 10, but this time, not only can two fluids be mixed, but also an incoming fluid in conjunction with a chemical mixture contained in cavity C'. In all other aspects the operation remains the same. FIGS. 11–13 also illustrate that the syringe may be pre-filled with separated solutions, and such solutions can be mixed through the simple withdrawal of the plunger. The solutions may be stored either in their mixed or separated condition for extended periods of time as for culture purposes, periodic slide work, and so forth. In connection with prefill usage, incorporation of the canula may be deleted.

What is thus provided is a multi-cavity syringe wherein the cavities or cylinder bores are axially oriented. A single plunger shaft is provided with a pair of pistons, a forward fixed piston and a rear floating piston. This structure is provided so that with the rearward actuation of the plunger shaft, the forward piston can be withdrawn as needed, with the rear piston remaining in a sealed, self-adjusting condition.

After a full withdrawal the two plungers may be linked together to move in tandem for an expression of contents, subsequent to the intermediate step of mixing the withdrawn fluid with any fluid or powder or other chemical disposed within the interior of the syringe prior to initial drawing in of fluid.

While particular embodiments of the present invention have been shown and described, it will be obvious to those skilled in the art that changes and modifications may be made without departing from this invention in its broader aspects, and, therefore, the aim in the appended claims is to cover all such changes and modifications as fall within the true spirit and scope of this invention.

I claim:

1. A device for mixing chemicals and including, in combination, a barrel having forward and rear contiguous bores of smaller and larger transverse cross-section and meeting at a common junction respectively, respective pistons disposed in said bores, and plunger means for linking said pistons for mutual, corresponding forward travel, said rear piston being in self-adjustment cooperation with said plunger for plunger withdrawal strokes, said barrel including bypass apertures shunting the junction of said forward and rear bores and spaced forwardly of said junction a distance greater than the axial thickness of said forward piston.

2. A syringe including, in combination, a barrel provided with coaxial, contiguous, forward and rear bores, said forward bore having a smaller transverse cross-sectional area than said rear bore, forward and rear pistons in slidable sealing arrangement with said bores, and an axially translatable plunger having a shaft axially coupled to and mounting said pistons, said rear piston including a central aperture in which said shaft is slidably disposed, said plunger shaft including a detent portion urgable rearwardly through said rear piston central aperture during times of plunger withdrawal, and thrust means engageable with said rear piston during forward plunger strokes for advancing said rear piston forwardly in tandem with said forward piston, a washer seated within said rear piston member, said washer having an eccentric aperture, said detent portion comprising a forwardly tapered enlarged portion constructed to radially displace said washer and slip through said eccentric aperture and also a forward surface for thrusting forwardly against said washer outwardly of said eccentric aperture to advance forwardly said rear piston.

* * * * *